United States Patent [19]

Sanderson et al.

[11] Patent Number: 4,867,916
[45] Date of Patent: Sep. 19, 1989

[54] ESTER MANUFACTURE

[75] Inventors: William R. Sanderson; John P. Sankey, both of Warrington, England

[73] Assignee: Interox Chemicals Limited, London, England

[21] Appl. No.: 128,109

[22] Filed: Dec. 3, 1987

[30] Foreign Application Priority Data

Dec. 5, 1986 [GB] United Kingdom ............... 8629208

[51] Int. Cl.$^4$ ............................................. C07C 69/76
[52] U.S. Cl. .................................... 260/402; 560/142; 560/109; 562/897
[58] Field of Search ............... 260/402, 410.5, 544 D, 260/544 Y, 545 R; 560/142, 109

[56] References Cited

U.S. PATENT DOCUMENTS

| | | | |
|---|---|---|---|
| 3,925,016 | 12/1975 | Haase | 8/169 |
| 4,587,054 | 5/1986 | Hardy et al. | 260/402 |
| 4,588,532 | 5/1986 | Moyne et al. | 260/402 |
| 4,704,236 | 11/1987 | Sankey et al. | 260/402 |

FOREIGN PATENT DOCUMENTS

| | | | |
|---|---|---|---|
| 105672 | 4/1984 | European Pat. Off. | |
| 120591 | 10/1984 | European Pat. Off. | |
| 125641 | 11/1984 | European Pat. Off. | |
| 0148148 | 7/1985 | European Pat. Off. | 260/402 |
| 153222 | 8/1985 | European Pat. Off. | |
| 153223 | 8/1985 | European Pat. Off. | |
| 0164786 | 12/1985 | European Pat. Off. | 260/402 |
| 0220656 | 5/1987 | European Pat. Off. | |
| 864798 | 4/1961 | United Kingdom | |

OTHER PUBLICATIONS

Püshel, Dr. F. and Todorov, Dr. O., "Connections between the Composition and Certain Properties of Surface Active Benzene Sulphonates with Heteroatoms in the Aliphatic Side Chain", Part 3: Preparation of Sulphonates, Tenside, 7, 1970, Heft 5, pp. 249-254, 1970; w/translation.

Primary Examiner—Bruce Gray
Attorney, Agent, or Firm—Larson & Taylor

[57] ABSTRACT

Phenol sulphonate esters can be made in a known process by reacting an alkali metal phenol sulphonate salt with an acyl halide in a hydrocarbon solvent at elevated temperatures, but the use of anhydrous materials were strongly advocated because any residual water hydrolyses the acyl chloride in a competitive reaction. However, it becomes particularly difficult and expensive to dehydrate phenol sulphonate salts below about 2% w/w water on a commercial scale and the product obtained by reaction from such partly dehydrated salts can be comparatively impure or reduced in yield. Consequently, changes to the process such as omitting the solvent or using a different acylating agent have been proposed, but these alternatives introduce their own respective manufacturing problems such as entrainment of viscous acyl chloride and anhydride in the product or introduction of a cumbersome and hence expensive recovery process involving an extra distillation step amongst others.

The present invention provides a surprisingly convenient modification to the known process in which the esterification and product separation steps are incorporated into a cycle together with an acyl halide preparation step in which residual carboxylic acid and anhydride in solution after product separation is preferably augmented with a replenishing amount of carboxylic acid and then reacted with thiony halide. The resultant ester is readily separable and is obtained in comparatively good yield.

18 Claims, No Drawings

ESTER MANUFACTURE

The present invention relates to a process for the manufacture of esters and in particular of phenol esters.

By way of background to the present invention, it will be recognised that within recent years there has been a trend in Europe for domestic clothes washing to operate at lower wash temperatures and in order to retain effective bleaching of stains considerable efforts have been made to incorporate bleaching agents or bleaching systems that are as active at the lower wash temperatures as conventional hydrogen peroxide/persalt bleaches have been at higher wash temperatures. Furthermore, an increased emphasis has been placed upon the incorporation or generation of bleaches that can act upon less hydrophilic stains, for example, relatively insoluble peroxyacids containing from 6 to 15 carbon atoms per peroxycarboxylic acid group.

Amongst those bleaching systems that were considered during an earlier period of intense activity, namely during the late 1950's and early 1960's, that system based upon acyloxybenzene sulphonates was the subject of considerable development. Although there was particular emphasis upon the acetoxy esters, British Pat. No. 864798 disclosed the preparation of the n-butyrate, caproate and caprylate esters of sodium phenol sulphonate by reacting excess of the aliphatic acid anhydride with anhydrous sodium phenol sulphonate at temperatures of from 120° to 200° C. for several hours. Such compounds can form the basis of bleaching systems which generate peroxyacids of intermediate hydrophilic/hydrophobic character and it was therefore natural that they or compounds similar to them should be given greater attention in recent years, especially in view of their favourable solubility compared with the corresponding derivatives of other favoured peroxyacid-generators such as tetra acyl ethylene diamine compounds.

As a result of the renewed interest in use of phenol sulphonate esters, there has been a resurgence of research into methods of preparing them, and especially the $C_6$ to $C_{15}$ esters. Some continued interest has remained with the use of acid anhydrides as for example by Rhone-Poulenc Chimie de Basee in EP-A No. 153222 and EP-A No. 153223 published 28th Aug. 1985. The reaction is carried out in a strong polar solvent, e.g. DMF so that it is necessary to add an anti-solvent, acetone, to the reaction mixture to remove the ester from solution and to separate the acetone and DMF before the solvent can be reused. Such a process accordingly introduces several additional processing steps which represent not only added capital and product-handling costs but also in the case of acetone separation an undesirable additional hazard. The Rhone-Poulenc specifications acknowledge that it might have been possible to employ an acyl chloride instead of the anhydride, but point to the slowness of reaction given in French patent specification No. 2 164 619 (equivalent to U.S. Pat. No. 3,925,016) and allege difficulty of separating the product from the reaction mixture and difficulties of eliminating HCl from the system. In an article by Pueschel (Tenside, 7(5) p 249–54) in 1970 in a similar process an acid acceptor pyridine and DMF are present, the solvent distilled off and the HCl is neutralised with sodium carbonate so that separation of sodium chloride from the ester poses a problem. If a higher temperature is used to increase the reaction rate, Rhone-Poulenc suggest that coloured impurities would be formed, and thus they invite the conclusion that the skilled man in the art would set the acyl chloride route on one side. It is interesting to note that whilst they do not specify that the phenol sulphate salt must be anhydrous they do submit it in their examples to a pre-reaction drying stage at 160° C. at high vacuum to 2600 pa, i.e. at about 1/40th atmospheric pressure. Clearly under such conditions substantially all water will have been removed.

The Procter & Gamble Company has described various methods for the manufacture of the esters. In EP-A No. 105672, they suggested that it is a conventional method to react the phenol sulphonate with an acyl halide in dioxan or dichloroethane, and indeed a similar route using chlorobenzene is followed by Procter in EP No. 120591 Example 1. The specification highlights the tendency for such a system to foam, caused by sparging to help remove the gaseous hydrochloric acid, and warns that unless the HCl is removed efficiently there is likely to be formation of the less stable sulphonic acid form of the ester and sodium chloride. It will be recognised that both are insoluble and solid and thus an extra separation step to separate the sodium chloride from the ester would be needed. Perhaps worst of all, Procter teaches that conversions in excess of 70% are difficult to obtain using an acyl halide. Instead, Procter advocates the use of a transesterification process in which a $C_2-C_3$ ester of phenol sulphonate is formed and then transesterified. The latter reaction is carried out using an excess of the higher molecular weight carboxylic acid as combined solvent/reactant. The specification alludes to potential problems of foaming during the transesterification and recognises that a further stage must in practice be introduced to separate residual carboxylic acid from ester product by dispersing the mixture in a solvent for the carboxylic acid which is a nonsolvent for the ester, such as liquid aliphatic or aromatic hydrocarbons. It is also of interest to observe that the process specified the use of anhydrous phenol sulphonate. Thus, such a process is cumbersome, requiring distillation by removing part of the excess reagents and a solvation technique to remove the rest. Moreover, there is an inevitable residue of undesired low molecular weight ester.

Subsequently, Monsanto in EP-A No. 148148 sought to improve a process based upon acyl chlorides. They state explicitly that the prior processes using acyl chlorides suffered from the need for expensive solvents, long reaction times and expensive separation/clean-up procedures. Moreover, if small amounts of solvent were used gelled reaction products would be obtained which are hard to separate and recover as a solid product. Instead, Monsanto advocates a solvent-free process employing excess acyl chloride. Throughout, they stress that anhydrous conditions be maintained. Whilst such a process appears at first glance to offer the inherent advantage of greater space yield the fluid is more viscous, having a greater tendency to entrain the evolved HCl and this also renders solid/liquid separation considerably more difficult, slower and expensive. There is also a corresponding tendency for the product to smell unpleasantly.

In EP-A No. 125641, Ethyl Corporation seeks to use a transesterification reaction between the phenol sulphonate and an alkyl aryl ester. They assert that although it is preferred that the process be carried out under substantially anhydrous conditions, it is not necessary for the reagents used to be anhydrous before they are combined since any water present in the reagents can be removed therefrom by conventional techniques such as by azeotropic distillation with an organic solvent such as hexane, octane, toluene, xylenes and the like. Strictly speaking, the technique comprises co-removal by entrainment of water in the solvent rather than the classical formation of an azeotrope. Ethyl Corp. in their Examples indeed demonstrate azeotropic solvent/water removal, but only on a small laboratory scale, dewatering less than 0.1 moles of sodium phenol sulphonate in each batch.

In EP-A No. 164786, Shell International Research address the problem of making a branched acyl ester of the phenol sulphonate and advocate the substitution of the potassium salt for the sodium salt in order to obtain products having a higher purity than the 84% obtained with the sodium salt. It is noteworthy that the main difference between the two salts is that the sodium salt is normally obtained in the form of a dihydrate and for use in esterifications has been dehydrated whereas the potassium salt is normally produced in anhydrous form so that the likelihood of residual water interfering with the reaction is much reduced. Shell insist that the sodium salt is dewatered before use, both in the text and in their comparative Example, and offer drying or azeotropic distillation as a suitable method. They employ an 18 hour drying stage at 150° C. under reduced pressure, 20 kPa, i.e. about 1/5th atmospheric pressure. The scale of the Examples was only 0.2 moles phenol sulphonate.

Summarising the disclosures in the prior specifications, it can be seen that many large and successful companies in the chemical field have expressed doubts concerning the desirability or viability of esterification of phenol sulphonates with acyl chlorides despite the fact that acyl chloride/aromatic alcohol reactions are commonly employed for laboratory scale preparations. In particular, emphasis is placed upon employing anhydrous reagents. However, we have found that the dehydration of sodium phenol sulphonate by azeotropy on a bulk scale poses tremendous difficulties in that the product tends to agglomerate and fuse together to form large lumps. These lumps interfere with the subsequent esterification, impairing not only the quality of the product but also the yield. In addition, it has been found that selection of appropriate esterification reaction conditions is of great importance in enabling a product to be obtained smoothly without problems of foaming or gelling or complete recovery of product referred to in the prior art.

There is an inherent attraction for processes that use any expensive reagent effectively and are simple to operate in terms of type and number of operations. Accordingly, further research effort has been directed to modifying the conditions for acyl chloride esterification of phenol sulphonate salts so as to better meet such objectives.

According to the present invention, there is provided a process for the production of esters of phenol sulphonate salts which comprises:

(1) an esterification step in which the phenol sulphonate is brought into contact with at least a stoichiometric amount of an acyl halide containing from 7 to 15 carbon atoms in the presence of sufficient solvent to dissolve the acyl halide, the solvent comprising an aliphatic hydrocarbon having a boiling point of at least 130° C., the mixture being maintained at a temperature of at least 120° C. until a substantial proportion of the phenol sulphonate has reacted with the acyl halide, and (2) a separation step in which the resultant solid ester of the phenol sulphonate is physically separated from the liquid phase, characterised in that the process includes (3) an acyl halide production step in which, after separation from the phenol sulphonate ester, the liquid phase is contacted with at least a stoichiometric amount of thionyl halide at a temperature of at least ambient up to the boiling point of the thionyl halide to convert any carboxylic acid and anhydride present to acyl halide for reaction with a further amount of phenol sulphonate, said carboxylic acid being present as a result of water released from the phenol sulphonate during the esterification step hydrolysing the acyl halide and said anhydride by further reaction of carboxylic acid with acyl halide.

Advantageously, it has been found that there is no need to indulge in lengthy or difficult drying//azeotropic dewatering procedures prior to the use of the phenol sulphonate salt in the invention process, in view of the fact that the reconversion of any carboxylic acid and/or anhydride produced as a by-product by hydrolysis can readily be achieved. Thus, it is possible to retain the ease of separation of the phenol sulphonate ester from the reaction mixture and introduce into the process a nearly quantitative use of the aliphatic acylating moiety without having to use totally anhydrous phenol sulphonates. The only significant loss of the aliphatic moiety from the reaction cycle, as distinct from recovery as part of the reaction product, is in the liquor retained by the separated product solids, i.e. filter-cake and even some of that can be recovered by washing the solids with additional or different solvent. It will be recognised that the present invention provides, therefore, a simple and effective process for making the ester which avoids high temperature distillation steps or reduced pressure drying operations that can be troublesome or time-consuming operations to carry out. By enabling readily available starting materials to be employed efficiently it represents a practical and commercially attractive method that the preceding acyl halide-based methods lacked.

From the foregoing, it will be recognised that the invention process can employ as phenol sulphonate salt, a material that has been only partially dehydrated. This is of considerable practical significance in that the conditions for water removal become increasingly more stringent and in particular require a disproportionately large amount of energy as the material approaches the anhydrous condition. Sodium phenol sulphonate is commercially available in an aptly named low water form, containing in the region of 2 to 4% w/w water. Such material is eminently suitable for use in the instant invention process, even though its use has been eschewed by previous ester producers.

With regard to step 1, the esterification step, it is especially suitable to employ a straight chain aliphatic acyl chloride containing from 6 to 15 carbon atoms, including specifically the acid chlorides of heptanoic acid, octanoic acid, nonanoic acid and decanoic acid. Such acyl chlorides have boiling points that permit reaction temperatures in excess of 130° C. to be employed. It has been found for such straight chain reactants that under optimum conditions yields and purities well in excess of 90% by weight based upon the phenol sulphonate can be obtained. Branched acyl chlorides of similar molecular weight such as 3,5,5-trimethyl hexanoic acid or 2-ethyl hexanoic acid can alternatively be employed but by virtue of their comparatively lower reactivity, a lower purity and yield is normally obtained than for the straight chain compound. Alternatively, it is possible to use instead, aryl acyl chlorides, including in particular benzoyl chloride. The acid bromides are alternatives.

The total amount of acyl halide employed, typified by acyl chloride is greater than one mole per mole of phenol sulphonate in order to allow for some hydrolysis of the acyl halide, and by virtue of the fact that the liquid phase containing it can be physically separated from the product at the end of the reaction, it is preferable to employ at least 1.2 moles per mole, often up to 5 moles per mole and especially from 1.5 to 3 moles per mole. The use of a substantial excess maximises the extent to which the insoluble reactant, the phenol sulphonate, can react. However, it is especially preferred to adjust the amount of the acyl chloride present such that substantially all of it is consumed in the reaction with either water or phenol sulphonate. As a result, the product separated in the next step is substantially free from residual acyl chloride and thus the malodour contributed by such a compound is absent. It is extremely beneficial in that the resultant product can thus be obtained not only in high yield and purity—in some cases of around 99% but also have a white appearance and be clean smelling. This objective is conveniently achieved by the use of 0.95 to 1.1 moles of acyl chloride per total number of moles of phenol sulphonate and water in the reaction mixture. It is possible for carboxylic acid generated by hydrolysis to react with further acyl halide to generate the corresponding anhydride. The residual amount of anhydride present at the end of the reaction tends to vary depending upon the extent to which acyl chloride was present in excess.

The reaction between the acyl halide and the phenol sulphonate generates one mole of hydrogen halide per mole of each reactant consumed. The phenol sulphonate is usually introduced with mixing into the solution of acyl chloride in solvent. The addition takes virtually no time on a small scale, but on a larger scale the period of introduction is often about 0.25 to 2 hours in order to obtain a stirrable well-dispersed mixture, during which period or subsequently, the temperature of the reaction mixture is brought up to the desired temperature. When the desired reaction temperature is reached, it is maintained for at least an hour and often up to 5 hours. A period of about 2 to 3 hours is preferred because that length of time is often sufficient to achieve virtually complete esterification of phenol sulphonates with a 50–100% molar excess of linear acyl halides.

During the reaction between acyl halide and phenol sulphonate, it is desirable to sparge the reaction medium with an inert gas such as nitrogen in order to facilitate the removal from the medium of gaseous hydrogen chloride or bromide. Sparging is assisted by the choice of aliphatic hydrocarbons or mixtures containing only a low proportion of aromatic hydrocarbon, thereby suppressing any tendency of the mixture to form a gelatinous product which can induce excessive foaming of the mixture with the consequential problems of control, likelihood of ejection of product from the reaction vessel and increased hazard.

The solvent employed in the invention can be any single aliphatic hydrocarbon having a boiling point of at least 130° C. normally up to 250° C. or, more conveniently, can be mixtures of aliphatic hydrocarbons of the appropriately high boiling point such as those obtained as fractions or cuts from the distillation of mineral oils. Cuts, having a median boiling point in the range of from about 140° to about 210° C. have been found to be extremely satisfactory. The solvent need not be 100% aliphatic, but a minor proportion of aromatic solvent can be tolerated, provided that it still meets the criterion of boiling at over 130° C. The proportion is preferably less than 25% v/v and particularly less than 10% v/v, so that it is possible to use solvents from which not all aromatic fractions have been removed.

If it is of practical benefit to employ enough solvent that the reaction mixture is always stirrable. Preferably the solvent weighs at least as much as the weight of phenol sulphonate, and more preferably is from one and a half to five times the weight of the phenol sulphonate. In many embodiments, this means that the weight ratio of solvent to residual anhydride/carboxylic acid/acyl chloride at the end of the esterification reaction period is in the range of 3:1 to 10:1.

It is especially suitable to employ an esterification reaction temperature of from 135° to 175° C., since by so doing the rate of reaction is maximised, which is of particular importance in the reactivity of branched acyl chlorides, whilst at the same time the likelihood of charring and production of a tar or oil is substantially eliminated.

The product can be conveniently separated from the reaction mixture by conventional solid/liquid separation apparatus such as a centrifuge, and the liquor can be recycled via step 3. The solid product retains inevitably some liquor. This can be removed at least partly by washing with solvent or acetone or dichloromethane. Since the bulk of the liquor retained in the cake consists of relatively cheap solvent there is a considerably reduced incentive to recover and recycle the liquor from any washings of the product cake, but to maximise efficiency of acid halide usage this may be done, if desired. In addition, since the solvent is essentially nonpolar the propensity of the liquor to retain the hydrogen halide is considerably reduced, with the result that the ester product has a reduced ionisable chloride or bromide impurity content.

It will be recognised that although the simple process described so far as regards steps 1 and 2 alone can, under some operating conditions be extremely efficient as regards phenol sulphonate usage, it is not as efficient when based upon acyl chloride/bromide usage. Since an acyl halide is of similar cost to low-water sodium phenol sulphonate it is clearly of commercial importance that both be employed efficiently. Advantageously, by incorporating the third step in the process the loss of expensive acyl chloride/bromide can be substituted by equimolar usage of a very much cheaper reagent, thionyl chloride/bromide. It would be possible to employ the third step in respect of solely that carboxylic acid and anhydride generated during the preceding step 1, but in a further and beneficial development of the process, step 3 can be used to make the entire requirement of acyl chloride by introducing extra carboxylic acid into the solvent/acid chloride/carboxylic acid and anhydride mixture prior to introduction of the thionyl chloride. Consequently the acyl chloride in such a process acts merely as a reactive intermediate in a cyclic process, the acyl reagent being introduced in carboxylic acid form, which is converted to the chloride which then reacts with the phenol sulphonate.

The analogous processes employing the acid bromide production from thionyl bromide and its subsequent use are also envisaged herein.

Advantageously it has been found that in the presence of the aliphatic hydrocarbon solvent there is no requirement to employ a catalyst, so that the process of step 3 can be effected merely by mixing thionyl chloride/bromide with the mixture containing the carboxylic acid. Conveniently the reaction can be carried out at ambient or elevated temperature. The mean and/or initial temperature is often in the range of 5° to 75° C.

It will be recognised that the reaction can take place at the subsisting temperature of the recycled liquor from step 2, either before or after dilution with additional carboxylic acid. In practice, the step 3 reaction temperature in many instances is from 20° to 50° C.

The reaction period of step 3 is usually at least 10 minutes and in practice is often selected in the range of 15 to 120 minutes. The amount of thionyl chloride/bromide introduced preferably approximates to the stoichiometric amount, i.e. 1 mole per mole carboxylic acid. A virtually quantitative reaction occurs. If on any cycle a small residue if unreacted carboxylic acid remains, the mixture can still be returned to the first step and reaction with further phenol sulphonate, the carboxylic acid acting at worst as a diluent.

The side products of the third step are both gaseous and thus do not readily contaminate the reaction mixture nor do they require any subsequent special separation procedures. Naturally, since they are acidic gases, it is environmentally prudent to absorb the gases in a suitable aqueous, preferably alkaline medium rather than vent them directly into the atmosphere.

It will be recognised that the gaseous by-products in steps 1 and 3 are acidic, containing HCl and in step 3 $SO_2$ as well. Thus, it is desirable to use reaction vessels and ancillary equipment that is made from material resistant to acid corrosion or contains a suitable lining. Metals such as certain grades of stainless steel and high nickel alloys and linings made from glass (vitreous enamel) and graphite tiles are well known in themselves.

The product of the instant invention process is a peroxyacid generator and can thus be incorporated in washing, bleaching or disinfecting compositions together with or for use in conjunction with a persalt or other hydrogen peroxide developing compound.

Having described the invention in general terms, specific embodiments will now be given in greater detail by way of example only of the method of the invention.

EXAMPLE 1

In this Example, a cyclic process is demonstrated in which the residual carboxylic acid and anhydride is reconverted to acid chloride and the balance is restored by addition of externally produced acid chloride.

Step 1

In the esterification step in the process, a recycle solution of nonanoyl chloride (108 g, 0.612M) dissolved in a mixed aliphatic hydrocarbon solvent being a fraction boiling between approximately 140° C. and 200° C., median 169° C. available under the trademark Shellsol D40 (213 g) was introduced into a three necked round-bottomed flask, equipped with stirrer and a nitrogen bleed, and over a period of about 30 minutes sodium phenol sulphonate (81.84 g, 0.408M, water content of 2.25%) was mixed in at ambient temperature. The reaction mixture was then heated to 155° C. and maintained at that temperature and mixed for 3 hours during which time the acid chloride progressively reacted with the sodium phenol sulphonate and water. It was observed that in excess of 90% of the acid chloride had been used up after 1 hour reaction so that a reaction period of that length would produce the greater bulk of the product, though at somewhat lower purity and efficiency of use of reagents than if the longer reaction period of preferably 2 to 3 hours is employed.

Step 2

At the end of the reaction period, the mixture was cooled to near ambient temperature and then filtered using a Buchner reduced pressure filter. The filter cake was washed with dichloromethane and dried. On analysis, it was found to comprise about 136 g (typically) of a white particulate sodium nonanoyl oxybenzene sulphonate of 99% purity and virtually free from smell.

Step 3

The filtrate (typically 197-199 g) was analysed and contained 27 g nonanoic anhydride and 1 g nonanoic acid. The residual acid chloride was below 2 g. The filtrate was then reacted with thionyl chloride(11.5 g, laboratory grade from BDH of 99% purity) an approximately equimolar amount for the anhydride and acid, at ambient temperature for 30 minutes, sparging off the sulphur dioxide and hydrogen chloride gas with nitrogen. The solution then contained approximately 33 g nonanoyl chloride (0.187M).

The solution was then restored by the addition of distilled acid chloride(0.415M, 75 g), and solvent (42 g approx) prior to its use for the next cycle.

EXAMPLE 2

In this Example, the procedures of steps 1 and 2 of Example 1 were followed. Step 3 was modified in that after analysis of the filtrate, fresh solvent (42 g) was added and nonanoic acid (0.415M, 65.6 g) was mixed in and then thionyl chloride (61 g, 0.51M) was reacted at slightly over ambient temperature (about 40° C.)for a period of about 3 to 4 hours.

The resultant solution was substantially the same as at the start of step 1, and was then recycled as in Example 1. The resultant sodium oxybenzene sulphonate salt similarly had a purity of 99% and a yield of typically 136 g.

Similar results were also obtained when a higher boiling point aliphatic hydrocarbon solvent mixture (Shellsol D60) was employed instead of Shellsol D40 solvent.

EXAMPLE 3

In this Example, the procedures of Example 2 were followed but employing 3,5,5-trimethyl hexanoic acid instead of nonanoic acid. A product of constant purity (about 83%) was obtained from 5 recycles and the efficiency of the reaction kept constant.

We claim:

1. In a process for the production of esters of phenol sulphonate salts which comprises:
   (1) an esterification step in which the phenol sulphonate is brought into contact with at least a stoichiometric amount of an acyl halide containing from 7 to 15 carbon atoms in the presence of sufficient solvent to dissolve the acyl halide, the solvent comprising an aliphatic hydrocarbon having a boiling point of at least 130° C., the mixture being maintained at a temperature of at least 120° C. until a substantial proportion of the phenol sulphonate has reacted with the acyl halide, and (2) a separation step in which the resultant solid ester of the phenol sulphonate is physically separated from the liquid phase, the improvement in the process which comprises including therein (3) an acyl halide production step in which, after separation from the phenol sulphonate ester, the liquid phase is contacted with at least a stoichiometric amount of thionyl halide at a temperature of at least ambient to convert any carboxylic acid and anhydride present to acyl halide for reaction with a further amount of phenol sulphonate, said carboxylic acid resulting from hydrolysis of the acyl halide by water released during esterification and said anhydride resulting from reaction of said carboxylic acid with acyl halide.

2. A process according to claim 1 characterised in that, steps (1), (2) and (3) form a cycle and between steps (2) and (3), sufficient carboxylic acid and/or anhydride is introduced into the reaction mixture to generate in step (3) said at least stoichiometric amount of acyl halide in step (1) in the succeeding cycle.

3. A process according to claim 1 characterised in that step (3) is carried out at a temperature of from 5° to 80° C.

4. A process according to claim 1 characterised in that the reaction period in step (3) is from 15 to 120 minutes.

5. A process according to claim 1 characterised in that thionyl chloride is employed in step (3).

6. A process according to claim 1 characterised in that the phenol sulphonate introduced in the esterification step, step (1), is a partly dehydrated sodium salt containing from 0.5% to 2% by weight water.

7. A process according to claim 1 characterised in that the phenol sulphonate salt is introduced in step (1) during a period of from 0.25 to 2 hours.

8. A process according to claim 1 characterised in that in step (1) the reaction mixture is maintained at the desired reaction temperature for at least an hour after the phenol sulphonate salt has been introduced, and preferably from 2 to 3 hours.

9. A process according to claim 1 characterised in that in step (1) the mole ratio of acyl halide to phenol sulphonate salt is from 1.0 to 5, and preferably from 1.2 to 2.0.

10. A process according to claim 9 characterised in that the mole ratio of acyl halide to the total of phenol sulphonate plus water in the reaction mixture in step (1) is from 0.95 to 1.1.

11. A process according to claim 1 characterised in that the carboxylic acid or anhydride employed is a linear aliphatic compound or an aryl compound.

12. A process according to claim 11 characterised in that the linear aliphatic compound is nonanoic acid and the aryl compound is benzoic acid.

13. A process according to claim 1 characterised in that the carboxylic acid or anhydride employed is a nonlinear aliphatic acid, preferably selected from 3,5,5-trimethyl hexanoic acid or 2-ethyl hexanoic acid.

14. A process according to claim 1 characterised in that the reaction mixture in step (1) is sparged during the reaction.

15. A process according to claim 1 characterised in that the amount of solvent employed is from 1.5 to 5 times the weight of phenol sulphonate salt.

16. A process according to claim 1 characterised in that the solvent contains less than 10% v/v aromatic hydrocarbons, and preferably virtually no aromatic hydrocarbons.

17. A process according to claim 2 characterised in that in step (1) a partly dehydrated sodium phenol sulphonate salt containing from 0.5 to 2% by weight of water is contacted with acyl halide in a mole ratio of halide to phenol salt of from 1.5 to 3 and to phenol salt plus water of from 0.95 to 1.1 for a period of 2 to 3 hours at a reaction temperature of 130° to 170° C.

18. A process according to claim 2 characterised in that in step (3) thionyl chloride is reacted at a reaction temperature of from 5° to 80° C. and for a reaction period of from 15 to 120 minutes with 3,5,5-trimethyl-hexanoic acid, 2-ethyl hexanoic acid, nonanoic acid, benzoic acid or their corresponding anhydrides.

* * * * *